United States Patent [19]

Zolton et al.

[11] Patent Number: 4,590,002

[45] Date of Patent: May 20, 1986

[54] METHODS FOR PREPARATION OF HIGHLY PURIFIED, GAMMA GLOBULINS FREE OF HEPATITIS-B-VIRUS INFECTIVITY

[75] Inventors: Raymond P. Zolton, Somerville; Paul M. Kaplan, Sergeantsville; John V. Padvelskis, S. Somerville, all of N.J.

[73] Assignee: Ortho Diagnostic Systems, Inc., Raritan, N.J.

[21] Appl. No.: 735,013

[22] Filed: May 17, 1985

Related U.S. Application Data

[63] Continuation-in-part of Ser. No. 680,191, Dec. 10, 1984, abandoned.

[51] Int. Cl.$^4$ .................... A61K 39/12; A61K 39/42; A61K 37/06; C07K 3/20
[52] U.S. Cl. .................................. 530/386; 424/89; 424/101; 530/387
[58] Field of Search .................... 260/112 B; 424/101, 424/89

[56] References Cited

U.S. PATENT DOCUMENTS 4,136,094  1/1979  Condie ................................ 260/122
4,434,093  2/1984  Zolton et al. .................... 260/112 B

OTHER PUBLICATIONS

Technical Bulletin 1075 of Bio-Rad Laboratories, 1975.
Tiollais et al., Science, 213 (1981), 406–411.
Hoppe, H. H. et al., Prevention of Rh-Immunization, Modified Production of IgG Anti-Rh for Intravenous Application by Ion Exchange Chromatography, Vox Sang 25:308–316 (1973).
Friesen, A. D. et al., Column Ion-Exchange Preparation and Characterization of an Rh Immune Globulin for Intravenour Use, J. Applied Biochem. 3:164–175 (1981).
Walsh, T. J. and O'Riordan, J. P., A Review of the Production and Clinical Use of Intravenous Anti-D Immunoglobulin, Irish Med. J. 75, 243–244 (1982).
Baumstark, J. S. et al., A Preparative Method for the Separation of 7S Gamma Globulin from Human Serum, Archives of Biochemistry and Biophysics 108:514–522 (1964).
Webb, A. J., A 30-Minute Preparative Method for Isolation of IgG from Human Serum, Vox Sang 23:279–290 (1972).
Stanworth, D. R., A Rapid Method for Preparing Pure Serum Gamma-Globulin, Nature 188:156–157 (1960).
Harris, et al., Freedom from Transmission of Hepatitis-B of Gamma-Globulin and Heat-Inactivated Plasma Protein Fraction Prepare from Contaminated Human Plasma by Fractionation with Solid-Phase Polyelectrolytes, Vox Sang 36:129–136 (1979).
J. M. Curling, Methods of Plasma Protein Fractionation, Pharmacia Fine Chemicals, Uppsala, Sweden, 1980 (Academic Press).

*Primary Examiner*—Howard E. Schain
*Attorney, Agent, or Firm*—Leonard Kean

[57] ABSTRACT

Methods for producing from human plasma or serum, human gamma globulin free of hepatitis-B-virus infectivity and products resulting therefrom. Specifically provided are ion exchange resin/buffer systems capable of effectively removing the virus.

13 Claims, No Drawings

METHODS FOR PREPARATION OF HIGHLY PURIFIED, GAMMA GLOBULINS FREE OF HEPATITIS-B-VIRUS INFECTIVITY

This application is a continuation-in-part of application Ser. No. 680,191, filed Dec. 10, 1984, now abandoned.

FIELD OF THE INVENTION

This invention relates to a process for the preparation of highly purified gamma globulins free of hepatitis-B-virus infectivity.

BACKGROUND OF THE INVENTION

Numerous medical conditions require treatment via injection of gamma globulin. The manner of preparation of the gamma globulin is of critical importance, particularly in order to eliminate the chance of contracting viral hepatitis. Viral hepatitis is a debilitating disease at best and lethal at worst. Consequently, any advances made to eliminate the chance of contamination of any injectable product by this virus are of immense importance.

Hepatitis B virus is estimated to infect approximately 200 million persons worldwide. Since the base material for the production of gamma globulins often is plasma obtained from a human source, the chances of obtaining contaminated or infected plasma are significant in view of the substantial number of persons who are chronically and acutely infected. The infected plasma from such a person may contain not only varying amounts of viral particles but also different sizes and forms of the particles. The most common form is the spherical particle which has a mean diameter of 22 nm. These spherical particles are devoid of DNA and represent free envelopes of the virus. Less common are the 42 nm Dane particles which represent the virion and consist of an envelope and a 27 nm nucleocapsid that contains a molecule of DNA. Free nucleocapsids may be observed in the nucleus of infected hepatocytes but are generally not found in the plasma. Infected hepatocytes have been found to synthesize excessive amounts of envelope which can be found circulating throughout the body. In accordance with the different components of viral particles, different immunological markers have been identified. For example, associated with the core is an antigen commonly labelled $HB_cAg$ and an "e" antigen labelled $HB_eAg$. The most common antigen employed for the detection of hepatitis B virus infection, however, is the surface antigen $HB_sAg$. The structure and genetic organization of the hepatitis viral particle has been reviewed in an article by Tiollais et al., in Biology of Hepatitis B Virus, Science, Vol. 213, 406–411 (July, 1981). Further discussion concerning the association of the Australian antigen with persistent or chronic hepatitis may be obtained in Australia Antigen and Hepatitis by Blumberg et al., C.R.C. Monotopic Series, C.R.C. Press, Cleveland, Oh. (1982). The close relationship of hepatitis B surface antigen to hepatitis viral infectivity is discussed by Blumberg, supra, on page 14.

Historically, a number of tests have been developed for the testing and identification of hepatitis-type viral infections and are uniformly directed towards the detection of hepatitis related antigens or the antibodies specific therefor. These tests have generally been characterized as a first, second or third generation test depending upon their sensitivity in the detection of weakly positive $HB_sAg$ reference panel samples obtainable from the U.S. Bureau of Biologics. Presently, the most sensitive tests available are of the third generation category and include radioimmunoassay, enzyme linked immunosorbent assay, reversed passive hemagglutination and reversed passive latex agglutination tests. Typical third generation immunoassays for $HB_sAg$ will detect approximately $10^9$ particles per ml of serum. Unfortunately, the primary particles to be detected are noninfectious 22 nm spherical forms. It is known that there is significant variation in the number of infectious Dane particles and noninfectious structures between sera. Therefore, sera can be diluted significantly past the point where they are positive in an immunoassay and still be infectious. See the article entitled "Hepatitis B virus infection in Chimpanzees, Titration of subtypes." in J. Infec. Dis. 132:451–459 (1975) by Barker et al. It thus becomes readily apparent that even a negative result with the most sensitive test available will fail to ensure the noninfectivity of a sample. Consequently, the manner of preparation for an immunoglobulin injectable reagent from a potentially infected plasma source becomes of paramount importance since any production method should ideally be capable of removing or destroying substantially all infective viral particles. At present, only in vivo chimpanzee studies are sufficiently sensitive to ensure noninfectivity of any particular sample. The cost and the requirements of such studies make them prohibitive for routine use. See "The Test for HB-Associated Antigens and Antibodies" by Gerety et al. in Chapter 11 of Viral Hepatitis, Ed. Vyas et al., The Franklin Institute Press, Philadelphia, Pa. (1978).

Presently, all immunoglobulin injectable materials approved for use by the FDA and Bureau of Biologics have been produced by the alcohol fractionation procedure developed by Dr. E. Cohn of Harvard during the 1940s and described in Cohn et al., J. Am. Chem. Sos., 68, 459 (1946). This procedure, coupled with the careful selection of plasma negative for hepatitis infectivity, determined by the most sensitive tests available, has been employed for such a long period of time (i.e., since the 1970's) that the U.S. government has adopted a position favoring only the resultant preparations of this procedure as safe. That the products produced by this procedure are indeed safe can easily be demonstrated by the millions of non-infected recipients of product. Unfortunately, occasional problems still arise demonstrating that despite the favorable appearance of the 'numbers' correlated with the Cohn process, the Cohn process still will not ensure complete noninfectivity. Despite the apparent success of the Cohn process to produce a safe human gamma globulin product, many investigators have attempted to find a replacement method which would involve fewer steps and milder conditions, offer higher yields and eliminate the presence of aggregates. The presence of the latter limits the current product to use for intramuscular injections only. The Cohn process is also disadvantageous because vast volumes of plasma are required due to the inherent low yield. Plasma is not only expensive but is also present only in limited supply.

It is an object of the present invention to provide a process whereby hepatitis B virus infectivity may be safely eliminated from a plasma by a more efficient process than that developed by Cohn et al. The resulting gamma globulin product would also be safe for both intramuscular or intravenous injections.

Several conventional methods for the separation of gamma globulin from human serum have been described notably by Baumstark et al. in "A Preparative Method For The Separation Of 7S Gamma Globulin From Human Serum", Archives of Biochemistry and Biophysics, 108, 514–522 (1964) and by A. J. Webb in "A 30-Minute Preparative Method For Isolation Of IgG From Human Serum", Vox Sang, 23:279–290 (1972). Although both of these papers are more concerned with the separation and selection of various gamma globulin classes from a serum containing numerous other contaminating proteins, they do address the removal of contaminating proteins and materials from the original serum sample. Both employ a DEAE-Sephadex column chromatographic material with a phosphate buffer eluting agent. Both investigators met with some degree of success as far as removal of contaminating proteins was concerned. However, both failed to address the problem of removing contaminating hepatitis viral particles in order to provide a safe, injectable reagent.

It is yet another object of the present invention to provide methods utilizing double chromatographic column resin/buffer combinations which are more effective in removing contaminating hepatitis viral particles than those provided by conventional methods.

Another method, described by Stanworth in an article entitled "A Rapid Method Of Preparing Pure Serum Gamma Globulin", Nature, 188, 156–157 (1960), involves the use of a diethyl amino ethyl cellulose anion exchanger to remove proteins from human serum dialyzed to remove high molecular weight proteins, however, the method described fails to account for the effect on hepatitis viral contaminants and additionally fails to provide an injectable reagent, both of which are objects of the present invention.

Condie has described in U.S. Pat. No. 4,136,094, "Preparation of Intravenous Human and Animal Gamma Globulins And Isolation Of Albumin", another method for obtaining gamma globulin which is claimed safe for intravenous administration. Condie's method involves three manipulations including plasma stabilization by treatment with fumed colloidal silica, isolation and elution of gamma globuin and albumin from ion exchange resins and finally concentration dialysis and sterile filtration. The fumed colloidal silica step is provided to remove hepatitis associated antigen present in the plasma as well as a number of proteolytic enzymes and their precursors. The colloidal silica treated materials were tested for presence of hepatitis associated antigen by radioimmunoassay. The materials tested negative and intravenous administration of large quantities (in excess of 30 g) in over 50 patients showed no evidence of passage of hepatitis virus nor produced cases of hepatitis. To be noted, however, as previously discussed, testing by presently available radioimmunoassay procedures will not ensure that the tested sample is free of infective hepatitis. Without further testing, any such material will not be approved by the U.S. government for widespread use in excess of that required for limited clinical studies. It is also to be noted that in the Condie process, there is a potential health hazard to workers due to exposure to silica fumes. The present invention avoids such exposure.

It is still another object of the present invention to provide a significantly simpler, effective procedure for isolating immunoglobulins from blood plasma and hepatitis associated antigens which does not require fumed colloidal silica.

Treatment of hemolytic disease of the fetus or newborn has become rather standard and is accomplished by treatment of the mother by injection of Rho (D) immunoglobulin of human origin. Such a product is RhoGAM, available from the assignee hereof, operates by preventing the unimmunized Rho (D) negative mother from responding to Rho (D) antigen present on red cells and 'received' at delivery from an Rho (D) positive infant. Thus, by preventing anti-Rho (anti-D) production by the mother at delivery, the subsequent Rho (D) positive infant of this mother is protected from hemolytic disease of the newborn. Although this successful product is presently produced by a Cohn alcohol fractionation type process, several investigators have attempted to use alternative methods to produce similar materials to thereby provide an economically more advantageous product and to reduce large plasma requirements. Such investigational efforts have been reported by Hoppe et al. in "Prevention of Rh Immunization Modified Production of IgG Anti-Rh For Intravenous Application By Ion Exchange Chromatography", Vox Sang, 25:308–316 (1973), Friesen et al. in "Column Ion-Exchange Preparation and Characterization of an Rh Immune Globulin for Intravenous Use", Journal of Applied Biochemistry, 3, 164–175 (1981), and Walsh, T. J. and O'Riordan, J. P. in "A review of the production and clinical use of intravenous Anti-D immunoglobulin", Irish Med. J. 75, 232–244 (1982).

Hoppe in Germany, Friesen in Canada and O'Riordan in Ireland, all employed a DEAE-Sephadex chromatography column in conjunction with a phosphate buffer eluding agent. Hoppe's source of anti-D containing plasma was from volunteers who passed an $HB_sAg$ laboratory test for at least six months, the plasma being stored in the interim. Thus, Hoppe employed a relatively safe, noninfective plasma to start with. Some screening work was done in Hoppe's laboratory to confirm the affinity of $HB_sAG$ for these resins. To our knowledge, no animal safety work was done to confirm removal of infectivity. Hoppe's concern was directed towards the removal of aggregated materials and the isolation of an unfragmented, immunoelectrophoretically pure IgG having a relatively high antibody concentration. The Freisen publication reports on the modifications made to the Hoppe method for the development of an intravenous Rh IgG for use in Canada. As Hoppe had done, Freisen tested each unit of Rh plasma for $HB_sAG$ to eliminate any donors testing positive. Freisen employed the radioimmunoassay kit from Abbott Laboratories, North Chicago, Ill. (Ausria II Kit). This test is still regarded as one of the most sensitive and was also employed in the development of the invention described later. Freisen reported that clinical trials showed the material produced using the DEAE-Sephadex resin/phosphate buffer combination was effective and safe for the prevention of Rh immunization. Freisen, however, reported no additional tests for determining the efficacy of the DEAE-Sephadex/phosphate buffer combination for removing hepatitis B virus infectivity from plasma samples. This, at least from the U.S. government's perspective, is especially important since the radioimmunoassay test employed in screening the donor plasma samples is incapable of detecting concentrations of $HB_sAG$ particles two or three orders of magnitude lower which may still be infective. It is this concern for the potential infectivity of a reagent produced by such a method that the U.S. government has been significantly more restrictive in permitting the production of injectable immunoglobulin reagents by ion-exchange methodologies.

It is an object of the present invention to provide resin/buffer systems that are superior in their ability to eliminate hepatitis B virus infectivity than those employed by previous investigators.

Zolton et al. in U.S. Pat. No. 4,434,093 have described methods for producing from human serum, human gamma globulin essentially free of $HB_sAg$. Specifically provided were single column "soft" ion exchange A-50 type resin/buffer systems capable of effectively removing $HB_sAg$ thought to be closely correlated with viral hepatitis type B infectivity. However, the "soft" resins used in U.S. Pat. No. 4,434,093 are not convenient for handling large volumes of plasma, thus creating "scale-up" difficulties. Furthermore, in view of the fact that only a single column was used in order to effectively remove $HB_sAg$, the ratio of A-50 resin per ml of applied sample was required to be no lower than 160 mg/ml to insure adequate removal of surface antigen. The resin used is extremely expensive and this is compounded by the fact that, for safety reasons, such resin should preferably be virgin and discarded after each trial.

It is an object of the present invention to provide double column resin/buffer systems which are better adapted for large-scale operation.

SUMMARY OF THE INVENTION

In accordance with the principals and objectives of the present invention, there are provided methods for the removal of substantially all hepatitis B virus infectivity from a gamma globulin containing body fluid that has most preferably been properly screened by third generation $HB_sAg$ tests. In addition such body fluid is most preferably adjusted by dialysis or dilution to match the running conditions (pH and conductivity) of the subsequent columns. The removal of the antigens is effectuated by the application of the body fluid to first and second columns in series. The first column contains an effective amount of a rigid resin consisting of DEAE-Sepharose CL-6B, DEAE-Sepharose CL-6B (Fast Flow) or DEAE Bio-Gel (High Capacity) and said second column contains an effective amount of a nonrigid resin consisting of DEAE-Sephadex or QAE-Sephadex. The body fluid is then eluted from the first column means with a buffer adjusted to a pH of at least 7.0, said buffer consisting of approximately 0.02 M phosphate buffer, if the resin selected for said second column means is QAE-Sephadex, or said buffer consisting of approximately 0.04 M Tris buffer, approximately 0.05 M imidazole buffer, or approximately 0.035 M sodium phosphate [$Na_2HPO_4$]-citric acid buffer, if the resin selected for said second column means is DEAE-Sephadex or QAE-Sephadex. The effluent from the first column is monitored for the presence of protein (preferably by optical measurement at 280 nm), those fractions containing protein being collected and pooled. This pooled protein is applied to the second column, the fluid from the second column being eluted with one of the buffers which may be utilized in said first column, the buffer being adjusted to a pH of at least 7.0. The second column effluent is then preferably monitored for the presence of protein. Thereafter, the effluent is collected responsive to protein monitoring whereby purified gamma globulin free of hepatitis-B virus infectivity is obtained. The diluted purified gamma globulin product in this effluent is then preferably concentrated by standard methods, for example, ultrafiltration, to produce a finished product.

It has been found that the effective amount of A-50 resin in said second column is an amount at least equal to 100 mg/ml of body fluid.

If a mixture of types A-25 and A-50 resin is used in the second column, it has been found that the effective amount of resin comprises a mixture of at least 27½ mg of A-25 type resin per ml of body fluid for every 80 mg of A-50 type resin per ml of body fluid.

Preferably the resin used in the second column comprises a mixture of 55 mg of QAE Sephadex type A-25 and 100 mg of QAE Sephadex type A-50 per ml of body fluid.

A preferred combination is one in which the resin in the first column is DEAE-Sepharose CL-6B and the buffer is approximately 0.05 M imidazole buffer; and the resin in the second column is QAE-Sephadex, the buffer used being approximately 0.05 M imidazole buffer.

The buffer utilized in each column is preferably adjusted to a pH of between 7.25 and 8.0, and most preferably to a pH of approximately 7.5.

DETAILED DESCRIPTION OF THE INVENTION AND BEST MODE

Because of the U.S. Government's justifiable concern regarding the safety of immunoglobulin preparations produced for injection into persons, the selection of the ion-exchange resins and eluting reagents is critical if eventual government-approved commercial production is to be realized.

In said Zolton et al. U.S. Pat. No. 4,434,093 (which patent is incorporated herein by reference), substantial in vitro tests were described. Because of the limited sensitivity of the best $HB_sAg$ detection tests available to date, a guiding evaluation principal is that any process employed to remove hepatitis B virus has to be shown to remove at least 3 orders of magnitude of infectivity to thereby bridge the gap between the sensitivity of the hepatitis B surface antigen test and the threshold of infectivity. In said Zolton et al. U.S. Pat. No. 4,434,093, the four tested resin buffer systems were QAE-Sephadex (A-50)/Tris, DEAE-Sephadex(A-50)/Tris, DEAE-Sephadex/Phosphate and QAE-Sephadex/Phosphate. It was shown in said U.S. Pat. No. 4,434,093, in which only one column was used, that the QAE-Phosphate, QAE-Tris and DEAE-Tris resin/buffer systems all reduced surface antigen concentration by approximately $10^5$ thereby providing an adequate safety factor assuming a 1:1 relationship between $HB_sAg$ concentration and infectivity. It was shown that the combination of DEAE-Sephadex/Phosphate buffer (which is representative of the prior art systems) was the least effective system in removing hepatitis B surface antigen since the concentration of $HB_sAg$ in the peak fraction after column treatment was at least 200 times greater than that in any of the other systems. It was also discovered in U.S. Pat. No. 4,434,093 that the ratio of "soft" A-50 type resin used per ml of applied sample should ideally be no lower than 160 mg/ml to ensure adequate removal of surface antigen.

This "soft" resin is very expensive, especially as it should preferably only be used once for safety reasons. In addition, the "soft" resin used in the single column shown in U.S. Pat. No. 4,434,093 is not really adaptable, on its own, for scaling-up purposes. In order to solve these problems, the present invention utilizes a double-column system, rather than the single-column system shown in U.S. Pat. No. 4,434,093. In the present method, a similar ion exchange resin/buffer system is used in the second column. In accordance with the present invention, there is provided a first column through which the plasma is passed. The first column contains a rigid resin which removes about 75% of plasma proteins such as albumin. This resin has excellent flow characteristics and can be used in large-scale column operations. In addition, this rigid resin can be regenerated many times (from 20 to 50 times) without loss of binding efficiency. Although the rigid resin is inadequate for the complete removal of $HB_sAg$, since some of the interfering proteins may be removed in the first column, the present invention enables the amount of A-50 resin in the second column to be reduced from 160 to 100 milligrams per ml of undiluted plasma, yet still providing adequate binding of the virus. Thus, the present system provides scale-up advantages and greater economy as compared to that of the Zolton et al.

U.S. Pat. No. 4,434,093. As pointed out above, albumin is removed in the first column as well as most of the other proteins, in accordance with the present process. In view of the removal of these proteins in the first column, the removal of the hepatitis-B-virus in the second column has been found to be much more efficient so that the effective amount of A-50 resin needed in the second column may be reduced, as stated above, to 100 mg/ml of body fluid.

It should be noted that the resin as well as the buffers used in the single column of U.S. Pat. No. 4,434,093 are the same as those used in the second column of the present process, the only difference being the quantity of resin used.

In view of the fact that the single column method of U.S. Pat. No. 4,434,093 was shown therein, by in vitro tests, to render human gamma globulin essentially free of $HB_sAg$, assuming proper screening of incoming units of blood, it is quite clear that the double column method of the present invention must be at least as effective or more effective than said single column method and accordingly, it is not deemed necessary to provide herein any in vitro test results with respect to said double column method. In summary, the earlier results in the Zolton et al. U.S. Pat. No. 4,434,093 showed that the use of certain resins and buffer systems have the ability to remove high amounts of $HB_sAg$ which is a known marker for viral hepatitis type B infectivity. Because of the prior economic limitations and scale-up problems, as well as the high cost of the resin, the present invention provides an improved system which utilizes two columns, the first column containing a rigid resin which has excellent scale-up properties which has been shown to be capable of being regenerated and reused multiple times. This rigid resin is used to remove the bulk of the protein such as albumin, although it is not used to remove a large amount of the hepatitis virus. The product from the first column, when passed over the second column containing a lower amount of soft resin (as compared to that used in the Zolton et al. U.S. Pat. No. 4,434,093), has a high ability to remove any virus which escaped from the first column. As pointed out above, for safety reasons, the resin in the second column should preferably be virgin and discarded after each trial. The pH and conductivity ranges specified in the Zolton et al. prior U.S. Pat. No. 4,434,093 have not been changed for the purposes of the present invention, with respect to the actual trials conducted.

Details concerning the chemical composition of the resins utilized in accordance with the present invention are as follows:

DEAE-Sepharose CL-6B, obtainable from Pharmacia Fine Chemicals, Uppsala, Sweden, is based on Sepharose CL-6B which is prepared by cross-linking a six percent (6%) agarose solution with epichlorohydrin, (agarose consists of repeating units of galactose and 3,6-anhydrogalactose). The gel is subsequently desulphated by alkaline hydrolysis under reducing conditions. The diethylaminoethyl (DEAE) group is then attached to the gel by ether linkages to the monosaccharide units of the Sepharose.

DEAE-Sepharose CL-6B (Fast Flow) which is also a registered trademark of Pharmacia Fine Chemicals, Uppsala, Sweden is similar to DEAE-Sepharose CL-6B except that the former is subjected to additional cross-linking.

DEAE Bio-Gel (high capacity) is a registered trademark of Bio-Rad Laboratories, Richmond, Calif. DEAE Bio-Gel is a cross-linked four percent (4%) agarose ion exchange gel. It is a weakly basic anion exchanger composed of diethylaminoethyl groups in the beaded agarose matrix. The expression "(high capacity)" merely signifies that it is produced for the commercial market.

DEAE-Sephadex, which is a registered trademark of Pharmacia Fine Chemicals, Uppsala, Sweden, is an anion exchanger produced by introducing the diethylaminoethyl (DEAE) functional group onto Sephadex which is also a registered trademark of Pharmacia Fine Chemicals. The DEAE group is linked to Sephadex through a stable ether linkage.

QAE-Sephadex, a trademark of Pharmacia Fine Chemicals, is an anion exchanger produced by introducing the quarternary amino ethyl (QAE) functional group onto Sephadex. The QAE group is attached to Sephadex through a stable ether linkage. Sephadex itself is a bead-formed gel prepared by cross-linking dextran with epichlorohydrin.

A limited in vivo study was conducted with three chimpanzees utilizing a material having a known infectious dose provided by the Bureau of Biologics. The purpose of the test was to confirm the safety claims of the new process. Details concerning the inoculum and preparation of plasma test sample as well as said in vivo study are as follows:

Inoculum and Preparation of Plasma Test Sample

Pre-Treatment Procedure

A well documented HBV infected inoculum ($HB_sAg$ subtype adr) was obtained from the United States Bureau of Biologics of the Food and Drug Administration. Starting infectivity was $10^5$ I.D./ml and the product was stabilized in calf serum and stored in the frozen state. Fresh human plasma was collected from each of 3 normal females and males and tested individually for $Hb_sAg$, anti-$HB_c$ and anti-$HB_s$ by RIA procedures. All six samples were found to be negative and the samples were pooled and then stored frozen. At the time of the trial both the inoculum and the normal plasma pool were thawed. The cold insolubles were removed from the latter by a standard centrifugation method. Next, one ml of the inoculum was added to nine ml of the cold insoluble supernate and the blend was well mixed. This step was done to simulate a more realistic sample since our purification process was not designed for calf serum. The mix was diluted equally with distilled water and the pH was adjusted with a few drops of 1.0 N HCl to 7.5±0.1. This sample was divided into two 10 ml portions. The first part (designated A) was used as the untreated specimen to be diluted later with albumin-saline buffer to be given to the control animal. The second part (designated B) was ready for application to the ion-exchange columns to produce the treated sample for the experimental animals, see description of purification process below.

Source of Ion-Exchange Resin

DEAE-Sepharose CL-6B® and QAE-Sephadex A-25 and A-50 were purchased from Pharmacia Fine Chemicals.

R-Trademark of Pharmacia Fine Chemicals, Uppsala, Sweden.

Buffer for Column Run

For both columns the buffer used was a 0.05 M imidazole-0.02 M sodium chloride. The pH was 7.5±0.1 and the conductivity was 2.2±0.4 millisiemens (5° C.). All reagents were of reagent grade and the source of each was Sigma (imidazole) and J. T. Baker (Sodium Chloride).

Chromatographic Systems for Column Runs

Two columns (0.9×15 cm. columns of acrylic plastic available from Pharmacia Fine Chemicals) were set up.

Column Run Procedure

The sample (designated B) scheduled for treatment was prepared as described above in the Pre-Treatment Procedure. Volume after pre-treatment was 10 ml and HBV infectivity was 5000 I.D./ml. The level of viral contamination was deliberately chosen so that at the point of application to column one, the sample would be weakly positive when tested by a third generation RIA procedure for $HB_sAg$. The trial, therefore represented an extreme challenge since this or higher levels of virus should not be encountered by a manufacturer who tests all in-coming units of blood. Prior to sample application, both columns were packed with appropriate swollen resin. The amount of DEAE-Sepharose CL-6B® in column one was at a ratio of one volume of resin (0.15 m Equiv.) for each volume of the initial plasma-virus mix. This resin had been exposed previously to three different loadings of uncontaminated diluted plasma and regenerated after each loading per the manufacturer's procedure. In column two, a mixture of virgin QAE-Sephadex resins A-25 and A-50 type were packed at a weight ratio of 55 mg of A-25 dry resin and 100 mg A-50 dry resin for each ml of the initial plasma-virus mix. The resin beds in both columns were flushed with buffer to establish a baseline $OD_{280\ nm}$ reading. The diluted plasma-virus mix was applied to column one at a flow rate of 105–115 cm/HR. After the applied sample had entered the resin bed, buffer was passed through the column. The effluent from the column was monitored for $OD_{280\ nm}$ reading and the product stream, rich in IgG, was collected when the baseline started to rise. The product collection continued until the baseline returned to an $OD_{280\ nm}$ value of 20–30% of the initial starting point.

The product volume was approximately twice its applied volume. This product was applied directly to column two and the same elution procedure was followed except the flow rate for this non-rigid resin was 50–55 cm/HR. The highly purified IgG product from this column experienced a 1.5 times increase in volume from application to column two.

Stabilization of the Untreated and Treated Products before Injection into the Animals The untreated sample was diluted with a pH 7.5 buffer comprised of 0.05 M Imidazole - 0.154 M sodium chloride-1.0% human albumin. Separately, this buffer was shown to be free of any hepatitis markers. After dilution, the untreated sample had an infectivity level of 20 I.D./ml.

The treated sample was diluted likewise so its final pH, conductivity and protein concentration would be similar to that of the untreated sample. After dilution, the infectivity level of the treated sample could be 1300 I.D./ml assuming no virus removal by the two column system.

Both diluted samples were stored in closed containers at 2°–8° C. for 48 hours before injection into the chimpanzees.

Chimpanzees

Three chimpanzees, numbers CH-344, CH-352 and CH-357, were studied. The control animal, CH-352 was 14 years old and weighed 59 Kgs at the start of the study. She had never been inoculated with HBV and had no serological markers for HBV infectivity. However, 14 months before this study, she was part of a HBV vaccine trial. She failed to respond but to avoid conflict with our study, she was used as the control. The experimental animals, CH-344 and CH-357, were both 2 years old and each weighed 11–12 Kgs at the start of the trial. These animals had never been part of any drug study and were free of any serological markers of HBV infectivity. All three animals were separately caged and the control animal was housed in a different building from the other two. Their human caretakers had received HBV vaccine shots and were tested frequently to insure absence of hepatitis.

Inoculations

Within two days of the fractionations the two final stabilized samples, treated and untreated, were administered to the animals. The control animal received 5.0 ml intravenously of the diluted untreated sample for a challenge of 100 I.D. Each of the experimental animals received 2.3 ml intravenously of the diluted treated sample for a potential challenge of 3000 I.D. None of the animals had any adverse effects to their intravenous injection.

Serological Studies

Serum specimens before and during the study were obtained and tested for alanine aminotransferase (ALT) by a spectrophotometer method with normal defined as ≦40 I.U/L, for $HB_sAg$, anti-$HB_s$, and anti-$HB_c$ by RIA methods purchased from Abbott Laboratories, North Chicago, Ill. Needle biopsies of the liver were performed on all three animals at frequent intervals throughout the study.

RESULTS

The control animal, CH-352, which received the untreated product, became infected by HBV and had $HB_sAg$ from weeks 25 to 29 inclusive, anti-$HB_c$ beginning at week 27 and anti-$HB_s$ beginning at week 33. ALT levels were elevated from weeks 27 to 29 inclusive with a peak value of 265 $IU/_L$. Further confirmation of the disease was obtained from the analysis of the needle biopsies (week 30).

The experimental animals, CH-344 and 357, which both received the treated product, remained free of infection throughout the nine months of the study. The serological and biopsy results were uneventful except for one observation early in the study for animal CH-344. She showed a positive anti-HB$_s$ value (3.8 S/N units) at eight weeks post inoculation. This result was not confirmed in twenty-two subsequent test samples. It has been concluded this result was an aberation.

The above study demonstrates that hepatitis B virus infectivity can be removed from human plasma used to prepare a gamma globulin product by the ion-exchange chromotography methods of the present invention.

Although the foregoing examples and trials illustrate the preferred mode of the instant invention, it is to be understood that the principles and scope of the invention are not to be so limited.

What is claimed is:

1. A method for removing hepatitis B infectivity from a gamma globulin containing body fluid comprising the steps of:
   (a) providing the gamma globulin containing body fluid desired to be purified;
   (b) applying the body fluid to first and second column means in series, said first column means containing an effective amount of a rigid resin consisting of DEAE-Sepharose CL-6B, DEAE-Sepharose CL-6B (Fast Flow) or DEAE Bio-Gel (High Capacity); and said second column means containing an effective amount of a non-rigid resin consisting of DEAE-Sephadex or QAE-Sephadex;
   (c) eluting the body fluid from said first column means with a buffer adjusted to a pH of at least 7.0, said buffer consisting of approximately 0.02 M phosphate buffer if the resin selected for said second column means is QAE-Sephadex, or said buffer consisting of approximately 0.04 M Tris buffer, approximately 0.05 M Imidazole buffer, or approximately 0.035 sodium phosphate [Na$_2$HPO$_4$]-citric acid buffer, if the resin selected for said second column means is DEAE-Sephadex or QAE-Sephadex;
   (d) monitoring the effluent from said first column means for the presence of protein;
   (e) collecting, responsive to monitoring, the protein containing effluent;
   (f) applying the collected protein containing effluent from said first column means to said second column means;
   (g) eluting the fluid from said second column means with one of said buffers which may be utilized in said first column means, said buffer being adjusted to a pH of at least 7.0, the buffers used in the first and second column means respectively, being the same or diferent; and
   (h) collecting the effluent from said second column means whereby any hepatitis-B-virus infectivity is now removed.

2. The method of claim 1 wherein the effective amount of resin in said second column means comprises a mixture of at least 27½ mg of A-25 type resin per ml of body fluid for every 80 mg of A-50 type resin per ml of body fluid.

3. The method of claim 2 wherein the resin in said second column means comprises a mixture of 55 mg of QAE Sephadex type A-25 and 100 mg of QAE Sephadex type A-50 per ml of body fluid.

4. The method of claim 1 wherein the effective amount of A-50 type resin when used alone in said second column means is an amount at least equal to 100 mg/ml of body fluid.

5. The method of claim 4 wherein the resin in said second column means is QAE-Sephadex and the buffer is 0.02 M phosphate buffer.

6. The method of claim 4 wherein the resin in said second column means is QAE-Sephadex and the buffer is approximately 0.04 M Tris buffer.

7. The method of claim 4 wherein the resin in said second column means is DEAE-Sephadex and the buffer is approximately 0.04 M Tris buffer.

8. The method of claim 4 wherein the resin in said second column means is QAE-Sephadex and the buffer is approximately 0.05 M Imidazole buffer.

9. The method of claim 8 wherein the resin in said first column means is DEAE-Sepharose CL-6B and the buffer is approximately 0.05 M Imidazole.

10. The method of claim 1 wherein the buffer in said first column means as well as in said second column means is approximately 0.05 M Imidazole buffer.

11. The method of claim 1 wherein the buffer is adjusted to a pH of between 7.25 and 8.00.

12. The method of claim 1 wherein the buffer is adjusted to a pH of approximately 7.5.

13. The method of claim 1, wherein the effluent from said second column means is first monitored for the presence of protein, before the protein containing effluent is collected responsive to said monitoring.

* * * * *

UNITED STATES PATENT AND TRADEMARK OFFICE
CERTIFICATE OF CORRECTION

PATENT NO. : 4,590,002
DATED : May 20, 1986
INVENTOR(S) : Zolton et al.

It is certified that error appears in the above-identified patent and that said Letters Patent is hereby corrected as shown below:

Claim 1, Col 12, line 4 delete "diferent" and insert

-- different --.

Signed and Sealed this

Second Day of September 1986

[SEAL]

*Attest:*

DONALD J. QUIGG

*Attesting Officer*  *Commissioner of Patents and Trademarks*